United States Patent
Baril et al.

(10) Patent No.: US 11,253,267 B2
(45) Date of Patent: *Feb. 22, 2022

(54) FRICTION REDUCTION MECHANISMS FOR HANDLE ASSEMBLIES

(71) Applicant: Covidien LP, Mansfield, MA (US)

(72) Inventors: Jacob C. Baril, Norwalk, CT (US); Brian J. Creston, West Haven, CT (US); Matthew A. Dinino, Newington, CT (US); Matthew Malavenda, West Haven, CT (US); Thomas A. Zammataro, Hamden, CT (US)

(73) Assignee: Covidien LP, Mansfield, MA (US)

(*) Notice: Subject to any disclaimer, the term of this patent is extended or adjusted under 35 U.S.C. 154(b) by 176 days.

This patent is subject to a terminal disclaimer.

(21) Appl. No.: 16/433,076

(22) Filed: Jun. 6, 2019

(65) Prior Publication Data
US 2020/0046363 A1    Feb. 13, 2020

Related U.S. Application Data

(60) Provisional application No. 62/718,019, filed on Aug. 13, 2018.

(51) Int. Cl.
*A61B 17/128* (2006.01)
*A61B 17/00* (2006.01)

(52) U.S. Cl.
CPC .. *A61B 17/128* (2013.01); *A61B 2017/00367* (2013.01); *A61B 2017/00477* (2013.01)

(58) Field of Classification Search
CPC . A61B 17/068; A61B 17/128; A61B 17/1285; A61B 2017/00367;
(Continued)

(56) References Cited

U.S. PATENT DOCUMENTS 3,120,230 A    2/1964 Skold
3,638,847 A    2/1972 Noiles et al.
(Continued)

FOREIGN PATENT DOCUMENTS

CN    103251441 A    8/2013
EP    0732078 A2    9/1996
(Continued)

OTHER PUBLICATIONS

International Search Report corresponding to Int'l Patent Appln. PCT/US2018/050316 dated Dec. 31, 2018.
(Continued)

*Primary Examiner* — Brooke Nicole Labranche
(74) *Attorney, Agent, or Firm* — Carter, DeLuca & Farrell LLP

(57) ABSTRACT

A handle assembly for actuating of a surgical end effector is provided. The handle assembly includes a friction reducing mechanism. The friction reducing mechanism may be mounted within a housing of the handle assembly and engage a drive member of the handle assembly. Alternatively, the friction reducing mechanism may be disposed on the drive member. The friction reducing mechanism instead or also includes a bearing member disposed between a trigger member and the housing of the handle assembly.

9 Claims, 12 Drawing Sheets

(58) Field of Classification Search
CPC .. A61B 2017/0046; A61B 2017/00477; A61B 2017/00845; A61B 2017/2919; A61B 2017/2947; A61B 17/2841; A61B 17/2909; A61B 2017/2925
See application file for complete search history.

(56) References Cited

U.S. PATENT DOCUMENTS

| | | |
|---|---|---|
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,336,458 A | 8/1994 | Hutchison et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |

(56) References Cited

U.S. PATENT DOCUMENTS

| | | |
|---|---|---|
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,824,547 A | 10/1998 | Hashino et al. |
| 5,824,548 A | 10/1998 | Hearn |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,044,971 A | 4/2000 | Esposito et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |

(56) References Cited

U.S. PATENT DOCUMENTS

| | | |
|---|---|---|
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,966,981 B2 | 11/2005 | Binder et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,446 B2 | 12/2005 | Hommann et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,597 B2 | 1/2006 | Gellman et al. |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,696 B2 | 1/2008 | Wilson, Jr. et al. |
| 7,585,304 B2 | 9/2009 | Hughett |
| 7,819,886 B2 | 10/2010 | Whitfield et al. |
| 7,905,890 B2 | 3/2011 | Whitfield et al. |
| 8,048,088 B2 | 11/2011 | Green et al. |
| 8,075,571 B2 | 12/2011 | Vitali et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,328,822 B2 | 12/2012 | Huitema et al. |
| 8,403,138 B2 | 3/2013 | Weisshaupt et al. |
| 8,419,752 B2 | 4/2013 | Sorrentino et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,753,356 B2 | 6/2014 | Vitali et al. |
| 8,821,516 B2 | 9/2014 | Huitema |
| 8,894,665 B2 | 11/2014 | Sorrentino et al. |
| 8,915,930 B2 | 12/2014 | Huitema et al. |
| 9,282,972 B1 | 3/2016 | Patel et al. |
| 9,445,810 B2 | 9/2016 | Cappola |
| 9,526,565 B2 | 12/2016 | Strobl |
| 9,717,504 B2 | 8/2017 | Huitema |
| 9,782,181 B2 | 10/2017 | Vitali et al. |
| 10,136,939 B2 | 11/2018 | Minnelli et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |

(56) References Cited

U.S. PATENT DOCUMENTS

| | | |
|---|---|---|
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0178813 A1* | 8/2005 | Swayze ............ A61B 17/07207 227/176.1 |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |

(56) References Cited

U.S. PATENT DOCUMENTS

| | | |
|---|---|---|
| 2008/0004639 A1 | 1/2008 | Huitema et al. |
| 2009/0204115 A1 | 8/2009 | Dees, Jr. et al. |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2010/0089970 A1 | 4/2010 | Smith et al. |
| 2010/0331862 A1 | 12/2010 | Monassevitch et al. |
| 2011/0087220 A1 | 4/2011 | Felder et al. |
| 2011/0087268 A1 | 4/2011 | Livneh |
| 2012/0022526 A1 | 1/2012 | Aldridge et al. |
| 2013/0041379 A1 | 2/2013 | Bodor et al. |
| 2013/0325057 A1 | 12/2013 | Larson et al. |
| 2014/0188159 A1 | 7/2014 | Steege |
| 2014/0276736 A1* | 9/2014 | Worrell .............. A61B 18/1445 606/33 |
| 2014/0371728 A1 | 12/2014 | Vaughn |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2017/0202567 A1 | 7/2017 | Griffiths et al. |
| 2017/0245921 A1 | 8/2017 | Joseph et al. |
| 2017/0252042 A1 | 9/2017 | Kethman et al. |
| 2017/0290587 A1 | 10/2017 | Schober et al. |
| 2018/0021041 A1 | 1/2018 | Zhang et al. |
| 2018/0263624 A1 | 9/2018 | Malkowski et al. |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | | |
|---|---|---|---|
| EP | 0755655 | A2 | 1/1997 |
| EP | 0769274 | A1 | 4/1997 |
| EP | 0769275 | A1 | 4/1997 |
| EP | 0834286 | A1 | 4/1998 |
| EP | 1317906 | A1 | 6/2003 |
| EP | 1609427 | A1 | 12/2005 |
| EP | 1712191 | A2 | 10/2006 |
| EP | 1813199 | A1 | 8/2007 |
| EP | 1908423 | A2 | 4/2008 |
| EP | 1913881 | A1 | 4/2008 |
| EP | 3132756 | A1 | 2/2017 |
| JP | 2011186812 | A | 9/2011 |
| JP | 2013166982 | A | 8/2013 |
| WO | 9003763 | A1 | 4/1990 |
| WO | 2005091457 | A1 | 9/2005 |
| WO | 2006042076 | A2 | 4/2006 |
| WO | 2006042084 | A2 | 4/2006 |
| WO | 2006042110 | A2 | 4/2006 |
| WO | 2008118928 | A2 | 10/2008 |
| WO | 2008127968 | A2 | 10/2008 |
| WO | 2017084000 | A1 | 5/2017 |
| WO | 2017146138 | A1 | 8/2017 |

OTHER PUBLICATIONS

International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.

* cited by examiner

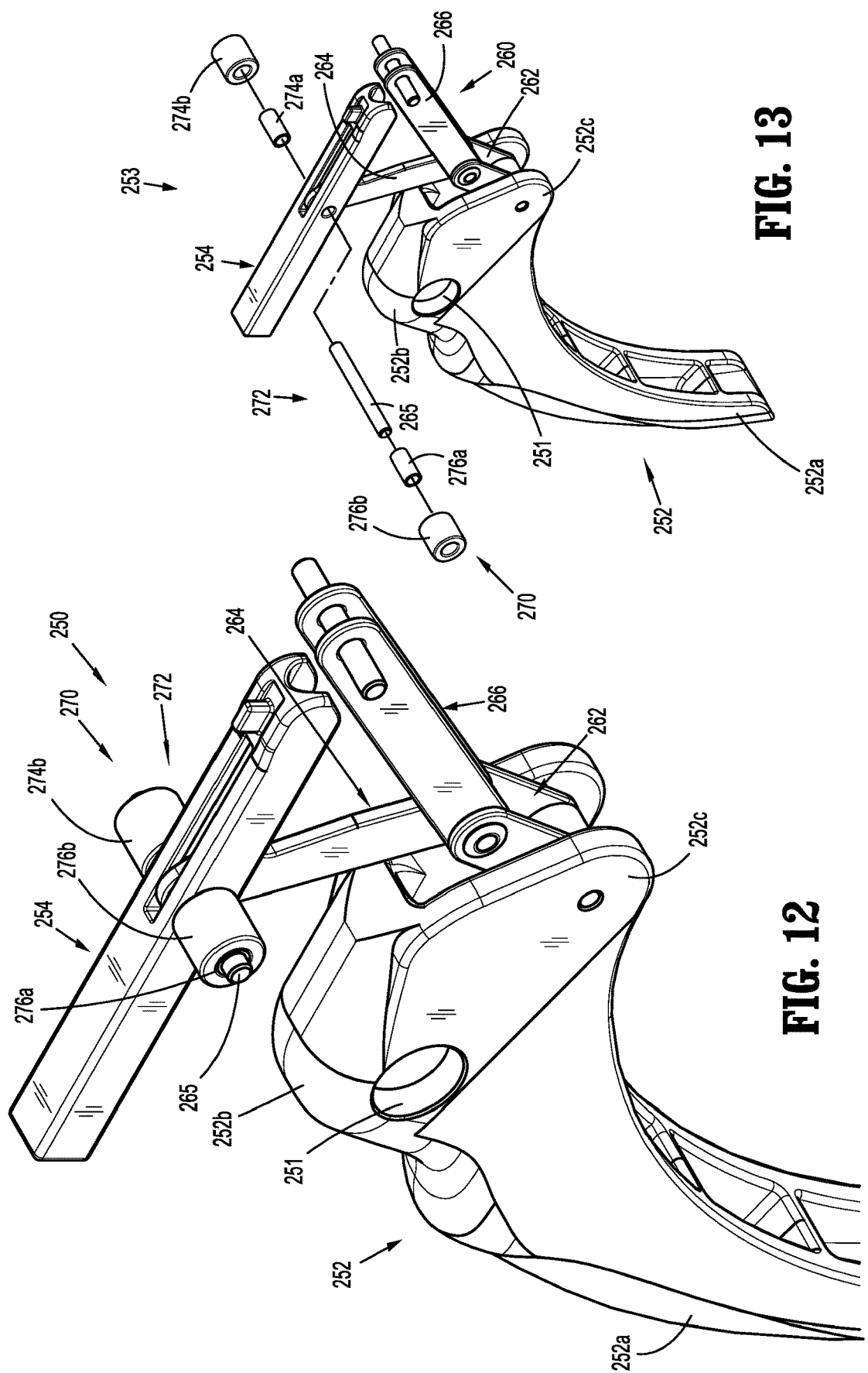

FRICTION REDUCTION MECHANISMS FOR HANDLE ASSEMBLIES

CROSS-REFERENCE TO RELATED APPLICATION

This application claims the benefit of and priority to U.S. Provisional Patent Application No. 62/718,019 filed Aug. 13, 2018, the entire disclosure of which is incorporated by reference herein.

BACKGROUND

Technical Field

The present disclosure relates to handle assemblies for surgical instruments. More particularly, the present disclosure relates to mechanisms for reducing friction experienced within the handle assemblies during firing strokes.

Description of Related Art

Handle assemblies are known in the medical art and are used for a number of distinct and useful surgical procedures. In the case of a laparoscopic surgical procedure, access to the interior of an abdomen is achieved through narrow tubes or cannulas that are releasably secured to the reusable handles inserted through a small entrance incision in the skin. Minimally invasive procedures performed elsewhere in the body are often generally referred to as endoscopic procedures.

Frictional forces experienced within the reusable handle during a firing stroke create wear on the handle assembly, thereby reducing its usable life. To extend the usable life of the handle assemblies, it would be beneficial to reduce the friction experienced within the handle assemblies during use.

SUMMARY

A handle assembly for actuating an end effector is provided. The handle assembly includes a housing defining a longitudinal axis, a trigger member operably coupled to the housing, a drive member movable within the housing along the longitudinal axis, a linkage assembly operably disposed within the housing and connecting the trigger to the drive member, and a friction reducing mechanism operably disposed within the housing relative to the drive member. The friction reducing mechanism includes first and second bearing assemblies. Each of the bearing assemblies including a sleeve rotatably disposed within the housing and configured to facilitate movement of the drive member.

In embodiments, the linkage assembly includes first, second, and third linkages. The linkage assembly may be moveable between an initial condition and a fully-actuated condition. The first bearing assembly may be positioned such that a longitudinal axis of the second linkage is tangent to the first bearing sleeve when the linkage assembly is in the initial condition. The second bearing assembly may be positioned such that the longitudinal axis of the second linkage is tangent to the second bearing sleeve when the linkage assembly is in the fully-actuated condition.

In some embodiments, the first bearing assembly includes a first pivot pin and the second bearing assembly includes a second pivot pin. The first and second bearing sleeves may be rotatably supported about the respective first and second pivot pins. The housing may include a pivot post and the friction reducing mechanism may include a third bearing sleeve. The third bearing sleeve may be received about the pivot post between the pivot post and the trigger member to reduce friction between the housing and the trigger member during actuation of the handle assembly.

Another handle assembly for actuating an end effector is provided. The handle assembly includes a housing defining a longitudinal axis, a trigger member operably coupled to the housing, a drive member movable within the housing along the longitudinal axis, a linkage assembly operably disposed within the housing and connecting the trigger to the drive member, and a friction reducing mechanism operably secured to the drive member. The friction reducing mechanism may include a bearing assembly having first and second outer bearing sleeves, and first and second inner bearing sleeves disposed within the respective first and second outer bearing sleeves and rotatably supported on a pivot pin. The first and second outer bearing sleeves engage the housing to facilitate movement of the drive member.

In embodiments, the housing defines first and second channels for receiving the respective first and second outer bearing sleeves. The housing may define first and second longitudinal slots for receiving respective first and second ends of the pivot pin. The pivot pin may extend transversely through the drive member. The linkage assembly may include first, second, and third linkages. The linkage assembly may be moveable between an initial condition and a fully-actuated condition.

In some embodiments, the bearing assembly is positioned to align with a longitudinal axis of the second linkage throughout actuation of the linkage assembly. The housing may include a pivot post and the friction reducing mechanism includes a bearing sleeve. The bearing sleeve may be received about the pivot post between the pivot post and the trigger member to reduce friction between the housing and the trigger member during actuation of the handle assembly.

BRIEF DESCRIPTION OF THE DRAWINGS

Aspects and features of the present disclosure are described in detail with reference to the drawing figures wherein like reference numerals identify similar or identical structural elements and:

FIG. 12 is back perspective view of the trigger, the drive member, the linkage assembly and the bearing assembly shown in FIG. 11;

FIG. 13 is back perspective view of the trigger, the drive member, the linkage assembly, and the bearing assembly shown in FIG. 11, with parts of the bearing assembly separated;

DETAILED DESCRIPTION

Figure 1:
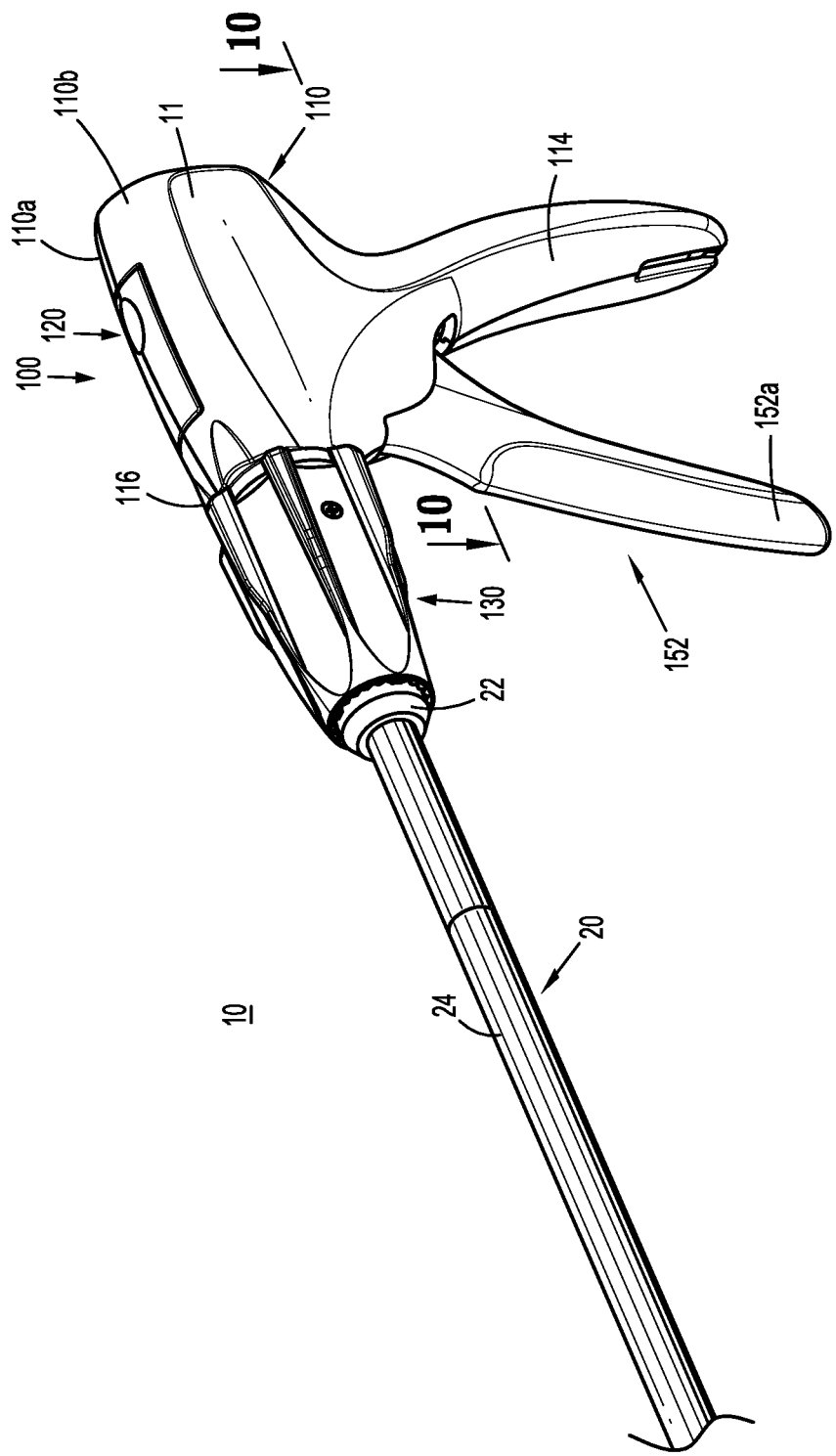
FIG. 1 is a front, perspective view of a surgical instrument provided in accordance with the present disclosure including a handle assembly having an elongated assembly engaged therewith.

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is farther away from the user. Further, to the extent consistent, any or all of the aspects and features detailed herein may be used in conjunction with any or all of the other aspects and features detailed herein.

The present disclosure provides friction reducing mechanisms for handle assemblies of surgical instruments. Although detailed herein as incorporated into surgical instruments, such as surgical clip appliers, the friction reducing mechanism of the present disclosure may be incorporated into any suitable surgical instrument, such as, for example, surgical staplers, surgical tack appliers, energy-based surgical devices, and the like.

Figure 2:
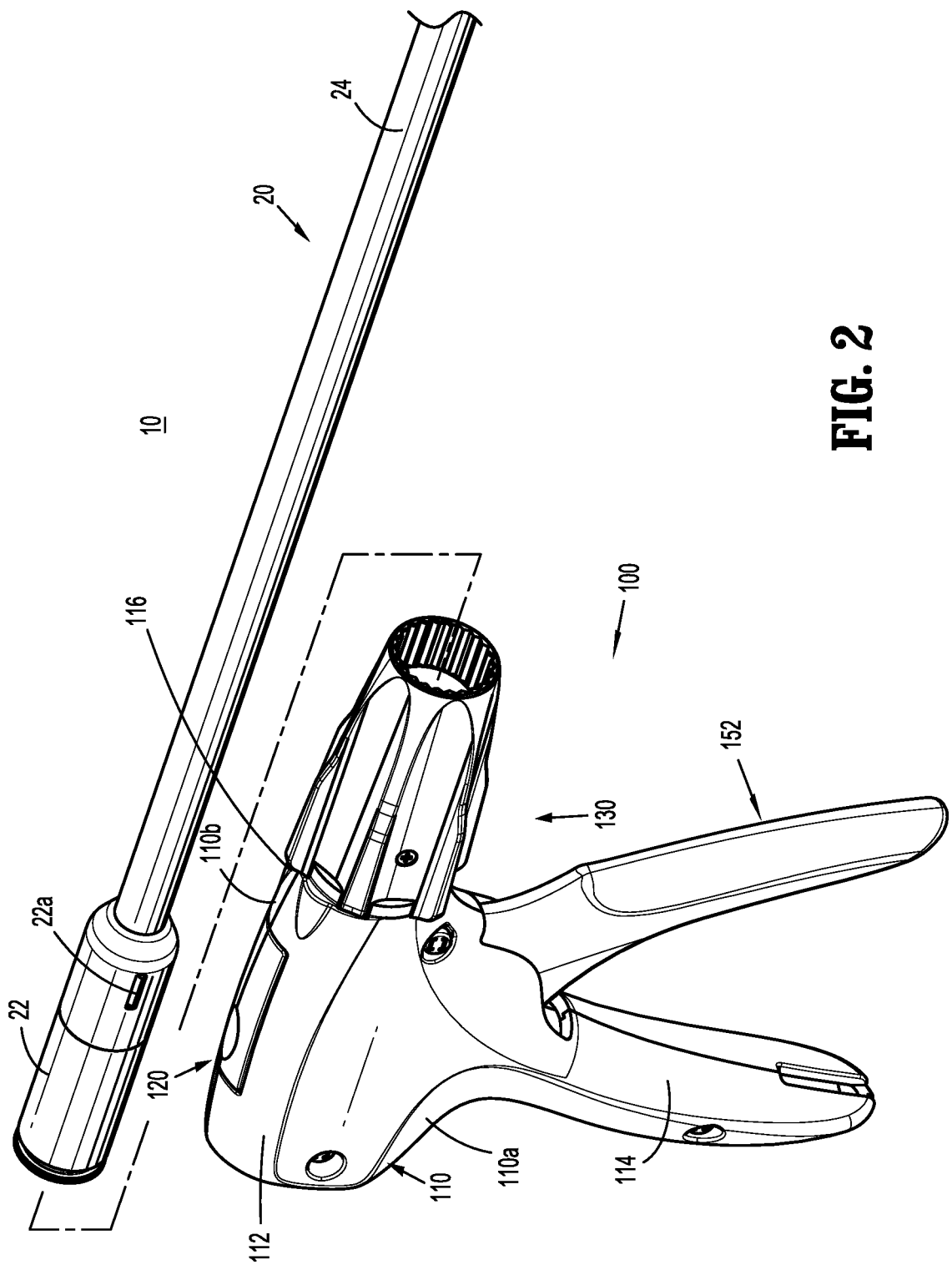
FIG. 2 is front, perspective view of the surgical instrument with the elongated assembly removed from the handle assembly.

Turning to FIGS. 1 and 2, a surgical instrument according to aspects of the present disclosure is shown generally as surgical instrument 10. The surgical instrument 10 generally includes a handle assembly 100 and an adapter assembly 20 selectively connectable to the handle assembly 100. The handle assembly 100 is configured to operate the adapter assembly 20 upon connection of the adapter assembly 20 to the handle assembly 100, and may be configured as a sterilizable, reusable component such that handle assembly 100 may be repeatedly used with different and/or additional elongated assemblies (not shown) during the course of one or more surgical procedures. The adapter assembly 20 may be configured as single-use disposable component, limited-use disposable components, or reusable components, depending upon a particular purpose and/or the configuration of the particular elongated assembly. In either configuration, the need for multiple handle assemblies 100 is obviated and, instead, the surgeon need only select an appropriate elongated assembly, and connect that elongated assembly to the handle assembly 100 in preparation for use.

The handle assembly 100 includes a housing 110, a latch assembly 120 (FIG. 3) operably disposed within housing 110, a rotation knob assembly 130 disposed on distal end of the housing 110, and an actuation mechanism 150 operably disposed within the housing 110. The housing 110 supports and/or encloses the operating components of handle assembly 100. The latch mechanism 120 is configured to facilitate releasable locking engagement of the adapter assembly 20 with the handle assembly 100. The rotation knob assembly 130 enables the selective rotation of the attached adapter assembly 20 relative to the housing 110. The actuation mechanism 150 is configured to enable selective firing of one or more surgical clips (not shown) from the end effector (not shown) of the attached adapter assembly 20. The end effector may be integrally formed with the adapter assembly 20, or may be a separate component releasably secured to the adapter assembly 20.

The handle assembly 100 will only be described to the extent necessary to fully disclose the aspects of the present disclosure. For a detailed description of the operation and function of an exemplary handle assembly, including exemplary latch and rotation knob assemblies, please refer to commonly owned U.S. Prov. Pat. App. Ser. No. 62/581,144 ("the '144 application"), filed Nov. 3, 2017, the content of which is incorporated herein by reference in its entirety. Other exemplary embodiments of handle assemblies may be found in commonly owned Intl. Pat. App. Nos. PCT/CN2016/096666 and PCT/CN2016/071178, filed on Aug. 26, 2016 and Jan. 18, 2016, respectively, the content of each is hereby incorporated herein by reference in their entirety.

Referring to FIGS. 1 and 2, the adapter assembly 20 of the surgical instrument 10 generally includes a proximal hub 22, an elongated shaft 24 extending distally from the proximal hub 22, an end effector (not shown) disposed towards a distal end portion of the elongated shaft 24, and an inner drive assembly (not shown) operably coupled between the handle assembly 100 and the end effector when adapter assembly 20 is engaged with the handle assembly 100, to enable the sequential firing of at least one surgical clip (not shown) about tissue. The end effector of the adapter assembly 20 may be configured to fire surgical clips similar to those shown and described in U.S. Pat. No. 7,819,886 or 7,905,890, the contents of each of which are hereby incorporated herein by reference in their entirety.

Figure 3:
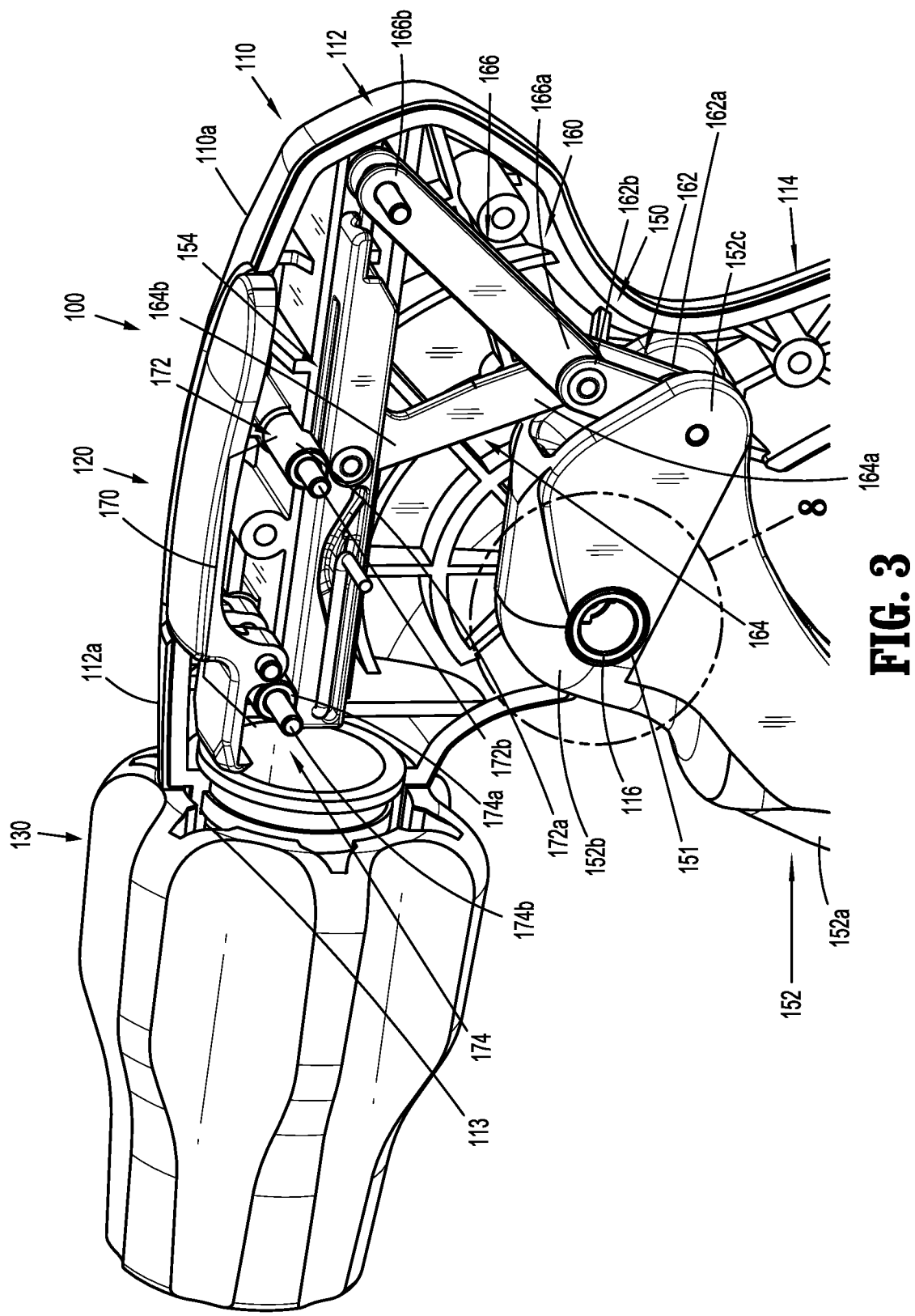
FIG. 3 is a side perspective view of the handle assembly of the surgical instrument shown in FIGS. 1 and 2, with a housing half removed exposing an actuation assembly.
Figure 4:
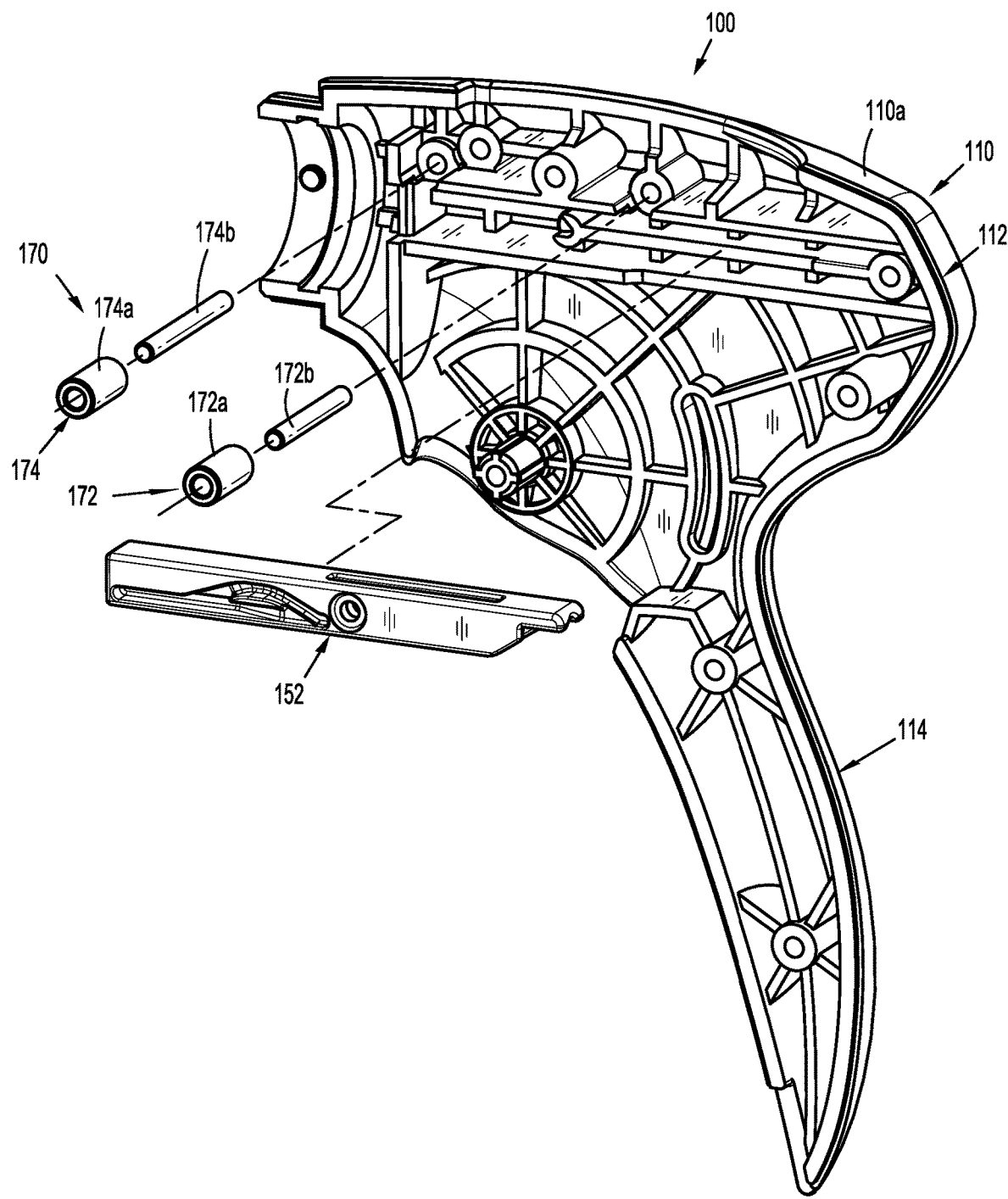
FIG. 4 is a side perspective view of a drive bar and bearing assemblies of the actuation assembly shown in FIG. 3, with parts separated.

With additional reference to FIG. 3, the housing 110 of the handle assembly 100 may be formed from first and second housing halves 110a, 110b that cooperate to define a body portion 112 and a fixed handle portion 114 depending from the body portion 112. The body portion 112 of the housing 110 includes a distal nose 112a defining a distal opening 113 (FIG. 3) therethrough. A proximal end portion of the proximal hub 22 of the adapter assembly 20 is configured to extend at least partially through the distal opening 113 of the distal nose 112a of the housing 110 when the adapter assembly 20 is engaged with the handle assembly 100.

The body portion 112 of housing 110 includes an internal pivot post 116 extending transversely within body portion 112.

The actuation mechanism 150 is operably supported by the housing 110 and includes a trigger member 152, a drive member 154 operably connected to the drive member 154 by a linkage assembly 160, and a friction reducing mechanism 170. As described below, the friction reducing mechanism 170 reduces the friction in the handle assembly 100, and provides a smoother firing sequence and a better mechanical advantage.

The trigger member 152 of the actuation mechanism 150 includes a grasping portion 152a, an intermediate pivot portion 152b, and a proximal extension 152c.

The grasping portion 152a of the trigger member 152 extends downwardly from the body portion 112 of the housing 110 in opposed relation relative to the fixed handle portion 114 of the housing 110. The grasping portion 152a is configured to facilitate grasping and manipulation of the trigger member 152.

The intermediate pivot portion 152b of the trigger member 152 is at least partially disposed within the housing 110 and defines a pivot aperture 151 that is configured to receive the pivot post 116 of the housing 110 so as to enable pivoting of the trigger member 152 about the pivot post 116 and relative to the housing 110, e.g., between an initial or pre-actuated position (FIG. 5), wherein grasping portion 152a of the trigger member 152 is spaced-apart relative to the fixed handle portion 114, and an actuated position (FIG. 6), wherein the grasping portion 152a of the trigger member 152 is approximated relative to the fixed handle portion 114.

The proximal extension 152c of the trigger member 152 is disposed on an opposite side of the intermediate pivot portion 152b of the trigger member 152 and, thus, opposite the pivot post 116, as compared to the grasping portion 152a of the trigger member 152. As such, pivoting of the grasping portion 152a to rotate in a first direction, e.g., proximally towards the fixed handle portion 114, pivots the proximal extension 152c to rotate in a second, opposite direction, e.g., distally.

The linkage assembly 160 includes a first linkage member 162, a second linkage member 164, and a third linkage member 166. The first linkage member 162 is pivotally coupled to the proximal extension 152c of the trigger member 152 towards a first end 162a of the first linkage member 162. The second and third linkages 164, 166 are each pivotally coupled to a second end 162b of the first linkage member 162 at first ends 164a, 166a of the respective second and third linkages 164, 166. A second end 164b of the second linkage member 164 is pivotally coupled to the drive member 154, while a second end 166b of the third linkage member 166 is pivotally coupled to the body portion 112 of the housing 110. Thus, the pivot point between the first linkage member 162 and the proximal extension 152c of the trigger member 152, the pivot point between the first linkage member 162 and second and third linkages 164, 166, and the pivot point between the second linkage member 164 and the drive member 154 are movable pivot points (e.g., movable relative to the housing 110), while the pivot point between the third linkage member 166 and the housing 110 is a fixed pivot point (e.g., fixed relative to the housing 110).

Upon actuation of the trigger member 152, e.g., proximal pivoting of the grasping portion 152a of the trigger member 152, the proximal extension 152c is moved in a counter-clockwise direction (from the orientation illustrated in FIG. 3), thereby urging the first linkage member 162 towards the drive member 154. This movement of the first linkage member 162 towards the drive member 154, in turn, urges the first ends 164a, 166a of the second and third linkages 164, 166, respectively, towards the drive member 154 to, in turn, urge the second end 164b of the second linkage member 164 distally such that the drive member 154 is translated distally through the body portion 112 of the housing 110, as indicated by arrow "A" shown in FIGS. 5 and 6. A biasing spring (not shown) may be provided to bias the trigger member 152 towards an initial or pre-actuated positon, thereby biasing the drive member 154 proximally.

The drive member 154 of the actuation assembly 150 is slidably disposed within the body portion 112 of the housing 110 in longitudinal alignment with the adapter assembly 20 when the adapter assembly 20 is engaged with the handle assembly 100. Distal sliding of the drive member 154 through the body portion 112 of the housing 110 during the firing stroke of the handle assembly 100 urges the drive member 154 into contact with a proximal portion (not shown) of inner drive sleeve (not shown) of the elongate assembly 20 to translate the inner drive sleeve distally, e.g., to apply, form or close a surgical clip supported on an end effector (not shown).

The friction reducing mechanism 170 of the actuation assembly 150 includes first and second sleeve bearing assemblies 172, 174. The first and second sleeve bearing assemblies 172, 174 include respective first and second sleeve bearings 172a, 174a supported by respective first and second bearing pins 172b, 174b within the body portion 112 of the housing 110. The first and second bearing assemblies 172, 174 of the friction reducing mechanism 170 facilitate distal movement of the drive member 154. More particularly, the first and second sleeve bearings 172a, 174a are rotatably supported about the respective first and second bearing pins 172b, 174b and are positioned to engage the drive bar 152. As the drive member 154 slides in a distal direction, the first and second sleeve bearings 172a, 174a rotate about the respective first and second bearing pins 172b, 174b thereby reducing the friction between the body portion 112 of the housing 110 and the drive member 154.

Figure 5:
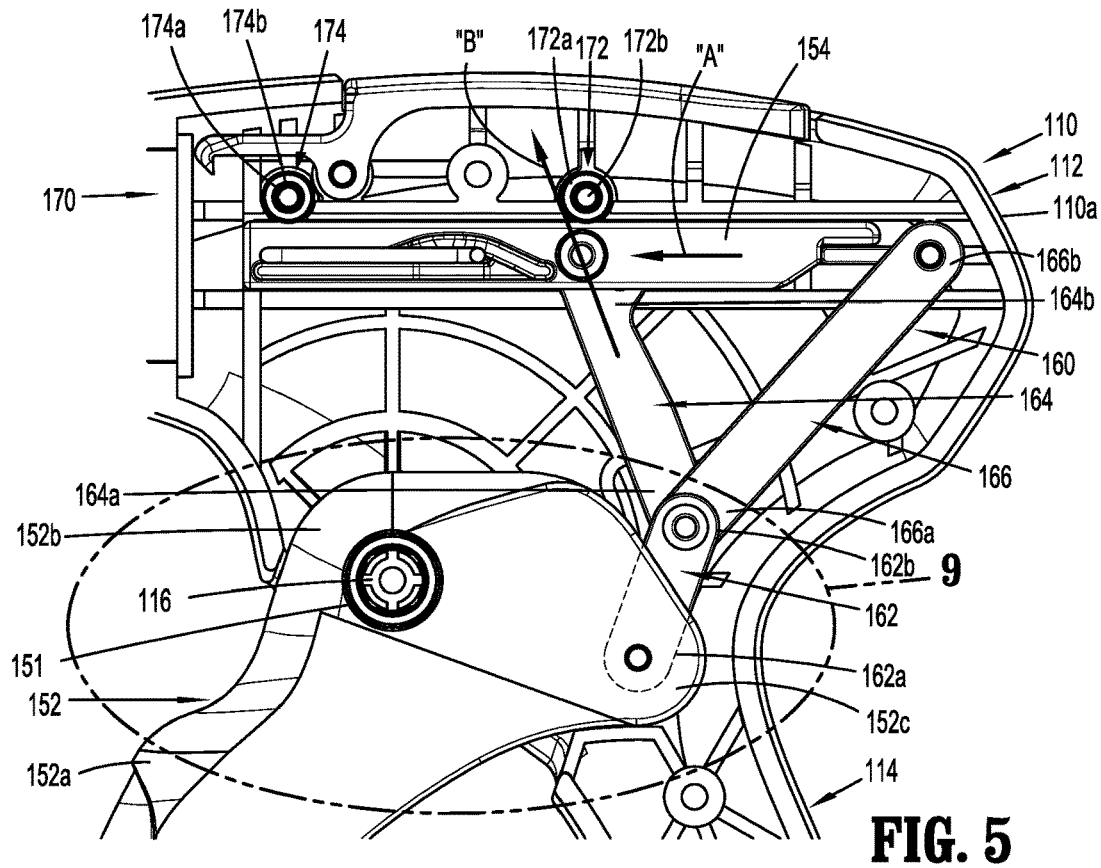
FIG. 5 is a side view of the handle assembly shown in FIG. 3, in a first or initial condition.
Figure 6:
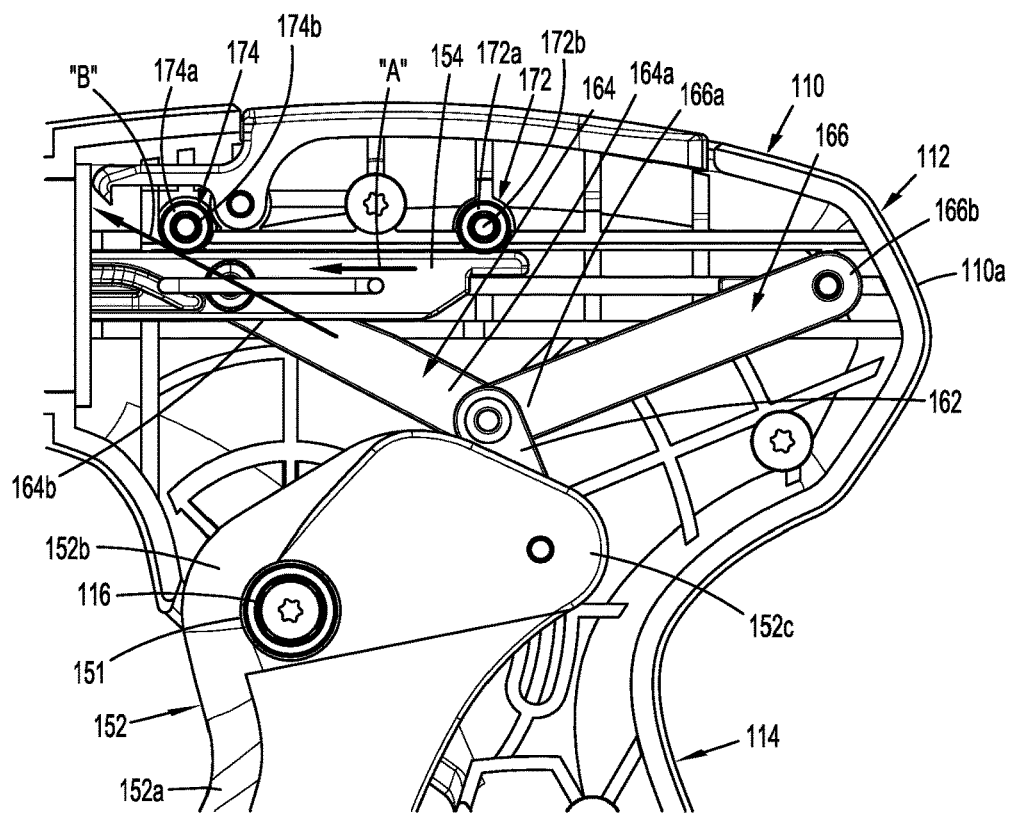
FIG. 6 is a side view of the handle assembly shown in FIG. 5, in a second or advanced condition.
Figure 7:
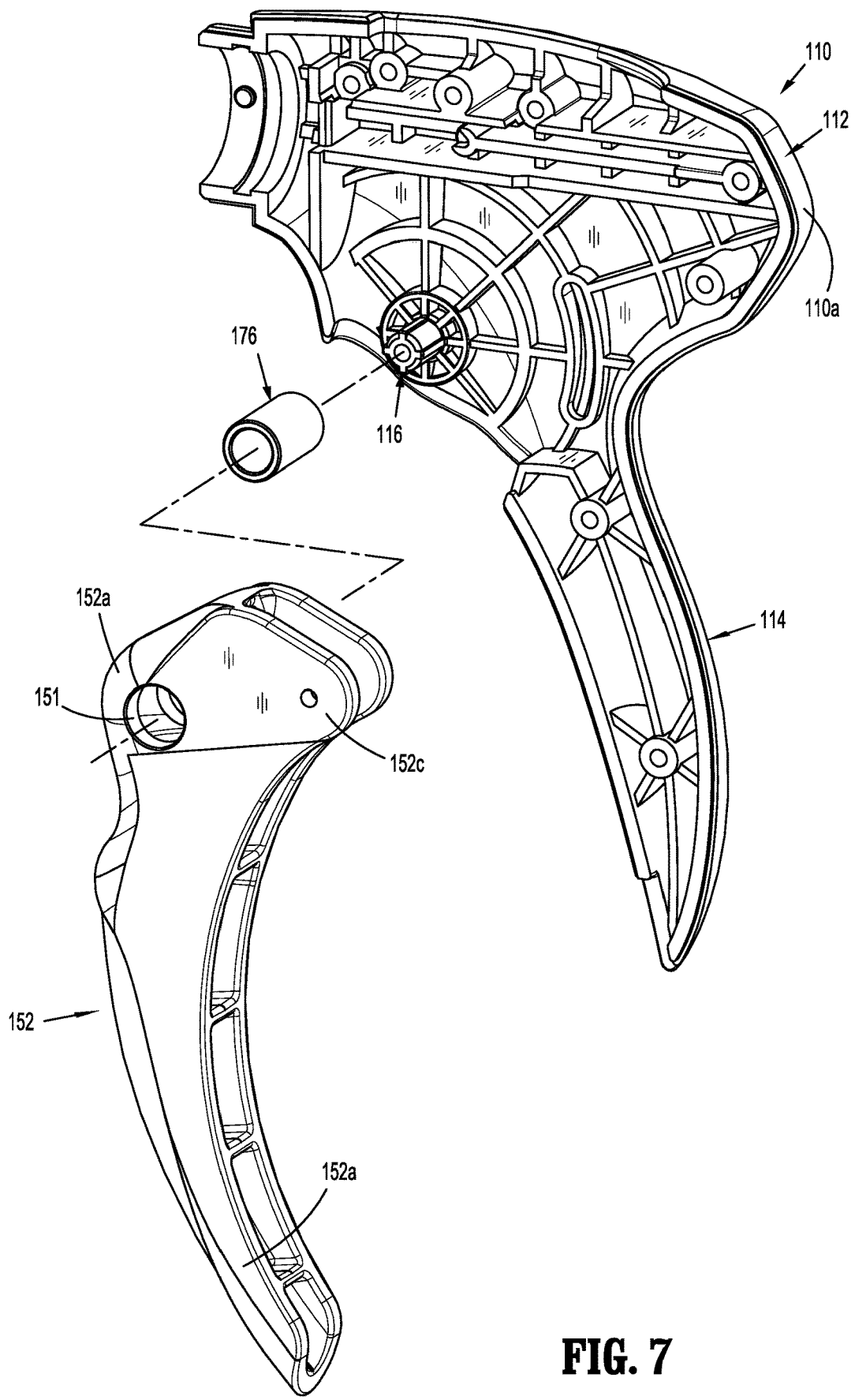
FIG. 7 a side perspective view of a trigger and a bearing assembly of the actuation assembly shown in FIG. 3, with parts separated.
Figure 8:
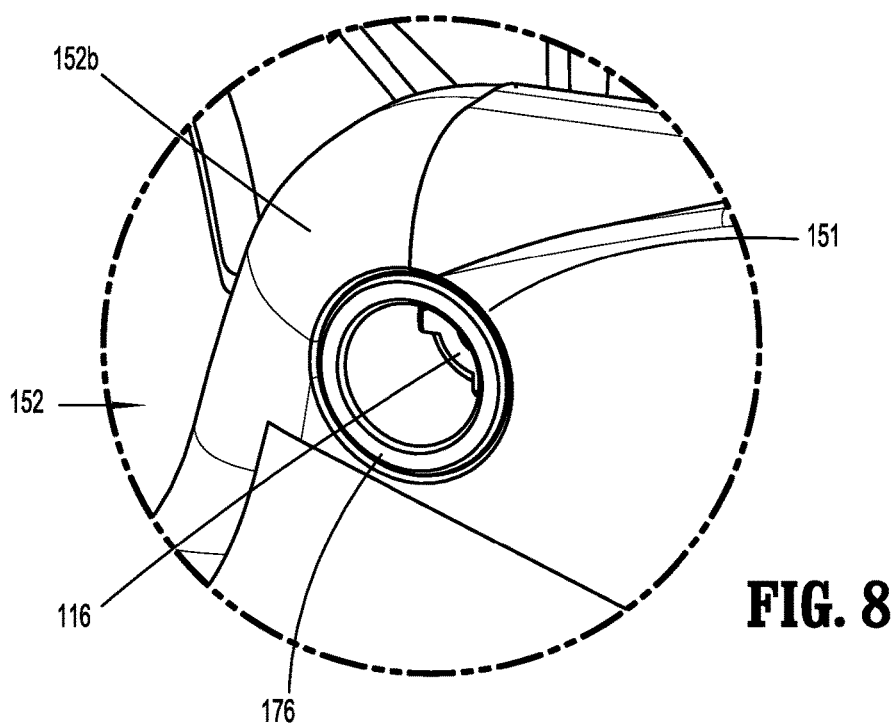
FIG. 8 is an enlarged view of the indicated area of detail shown in FIG. 3.
Figure 9:
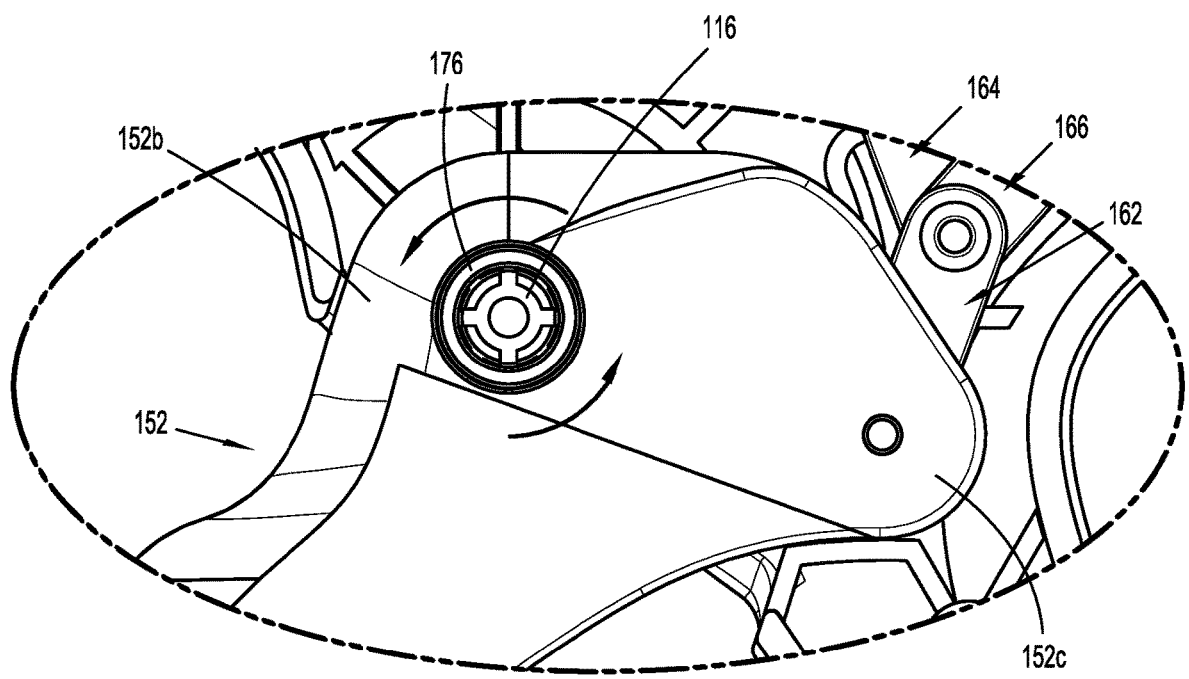
FIG. 9 is an enlarged view of the indicated area of detail shown in FIG. 5.
Figure 10:
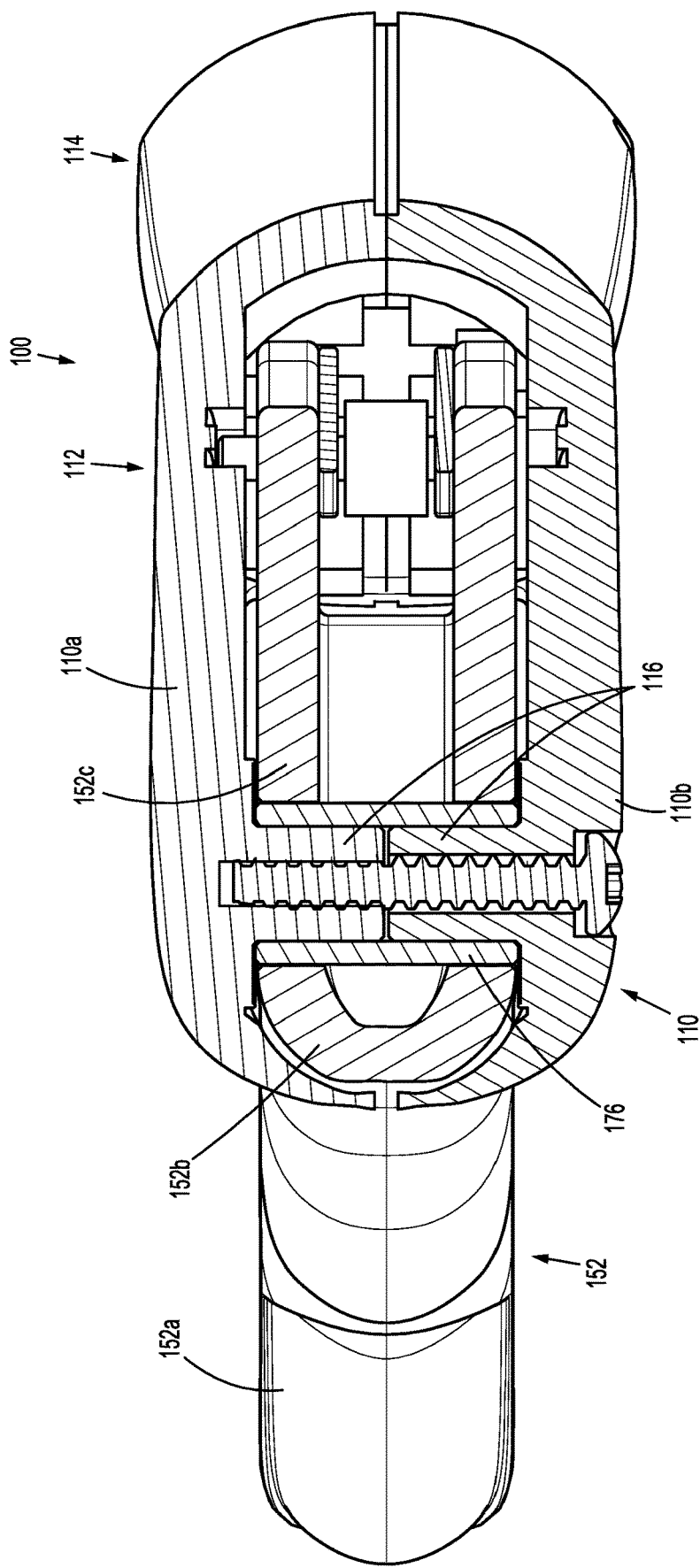
FIG. 10 is a cross-sectional top view taken along line 10-10 shown in FIG. 1.
Figure 11:
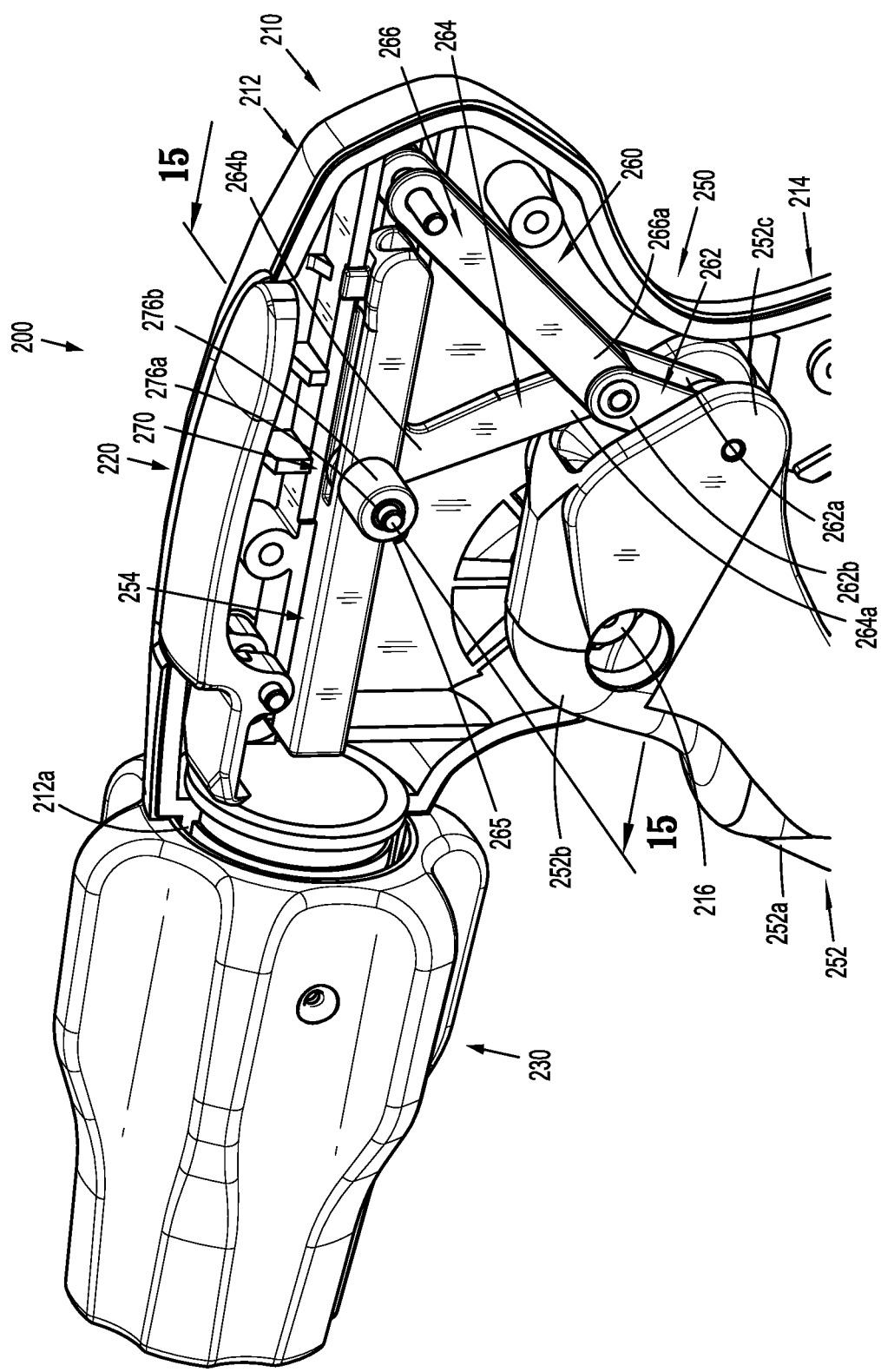
FIG. 11 is a side perspective view of a handle assembly of according to another embodiment of the present disclosure, with a housing half removed exposing an actuation assembly including a trigger, a drive member, a linkage assembly, and a bearing assembly.
Figure 15:
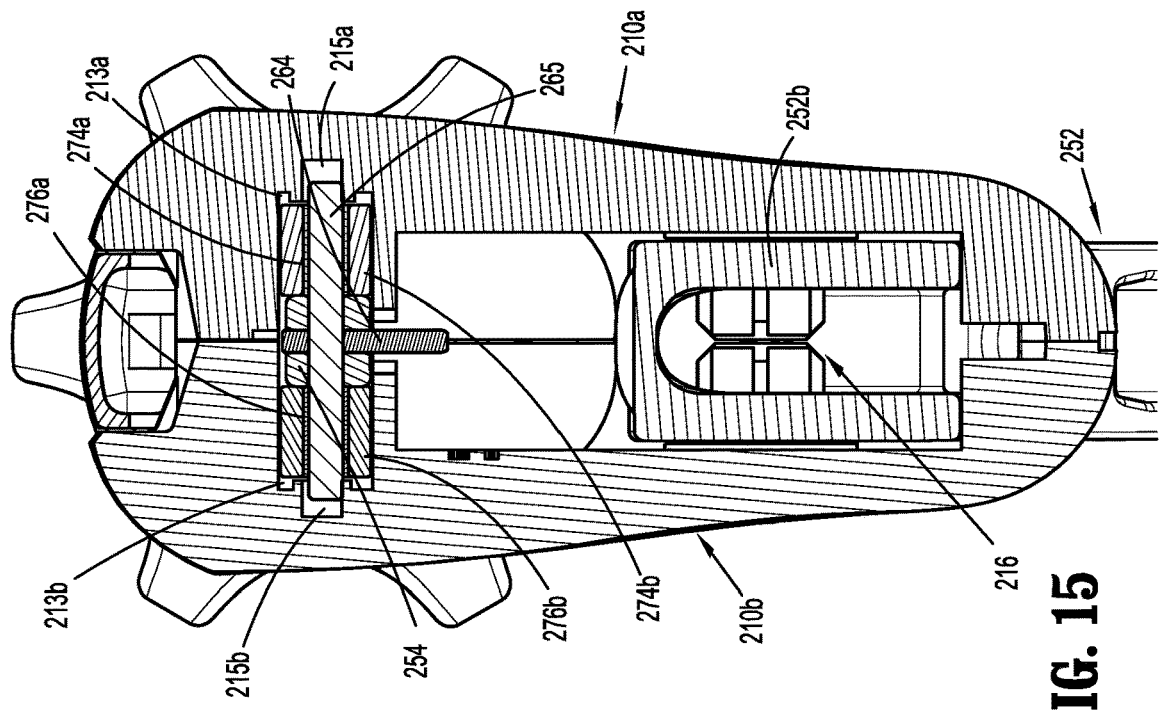
FIG. 15 is a cross-sectional end view of taken along line 15-15 shown in FIG. 11.
Figure 14:
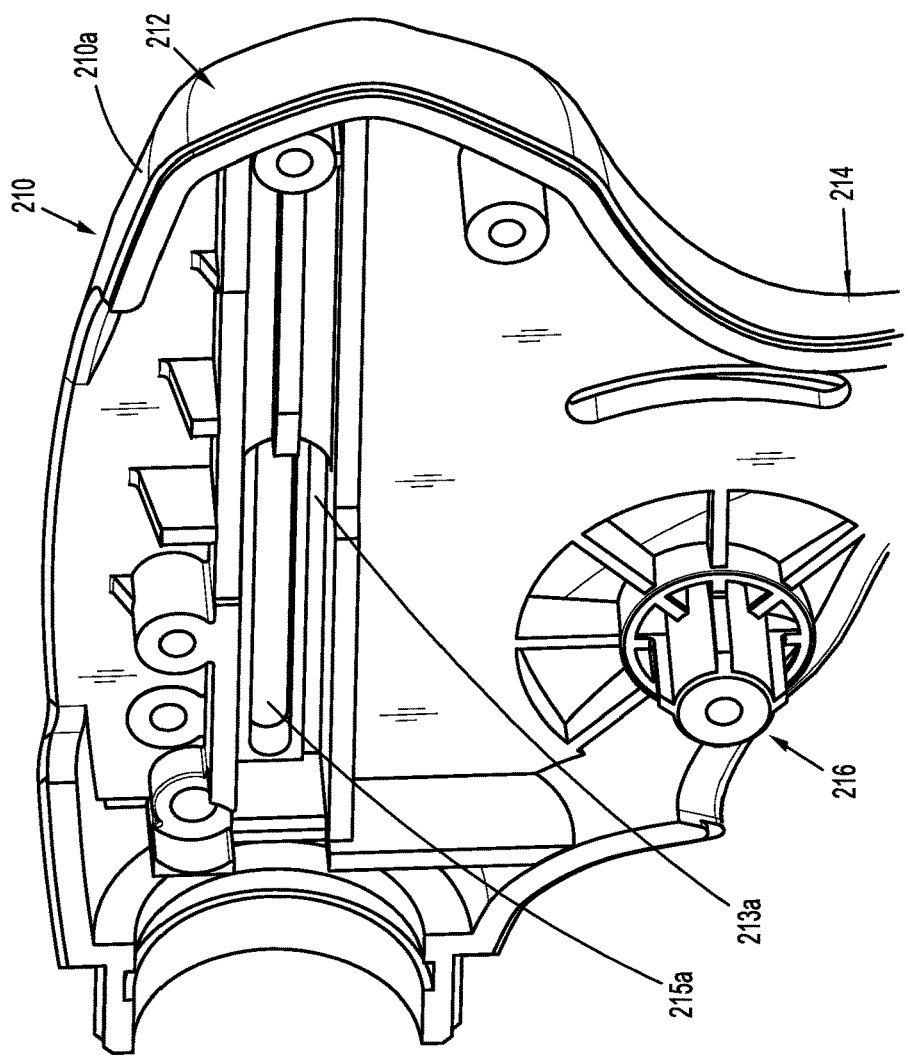
FIG. 14 is a side perspective view of the housing half shown in FIG. 11.
Figure 16:
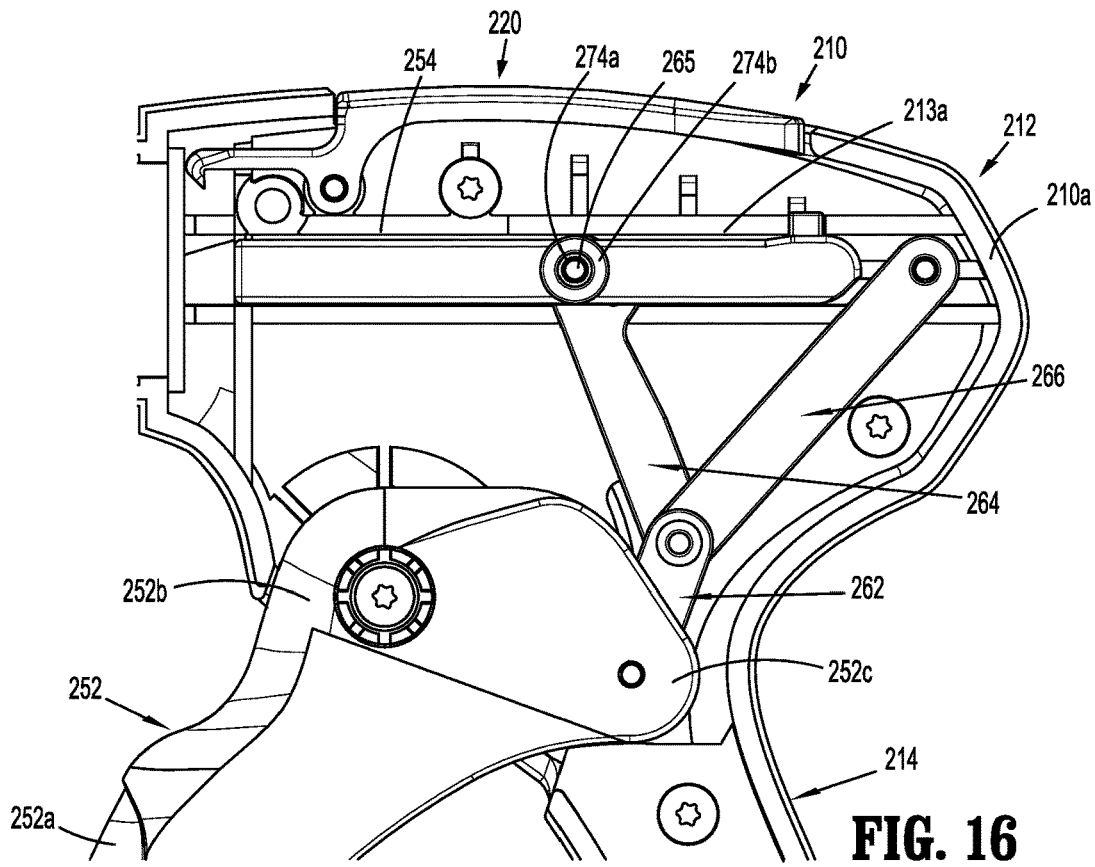
FIG. 16 is a side view of the handle assembly shown in FIG. 11, in a first or initial condition.
Figure 17:
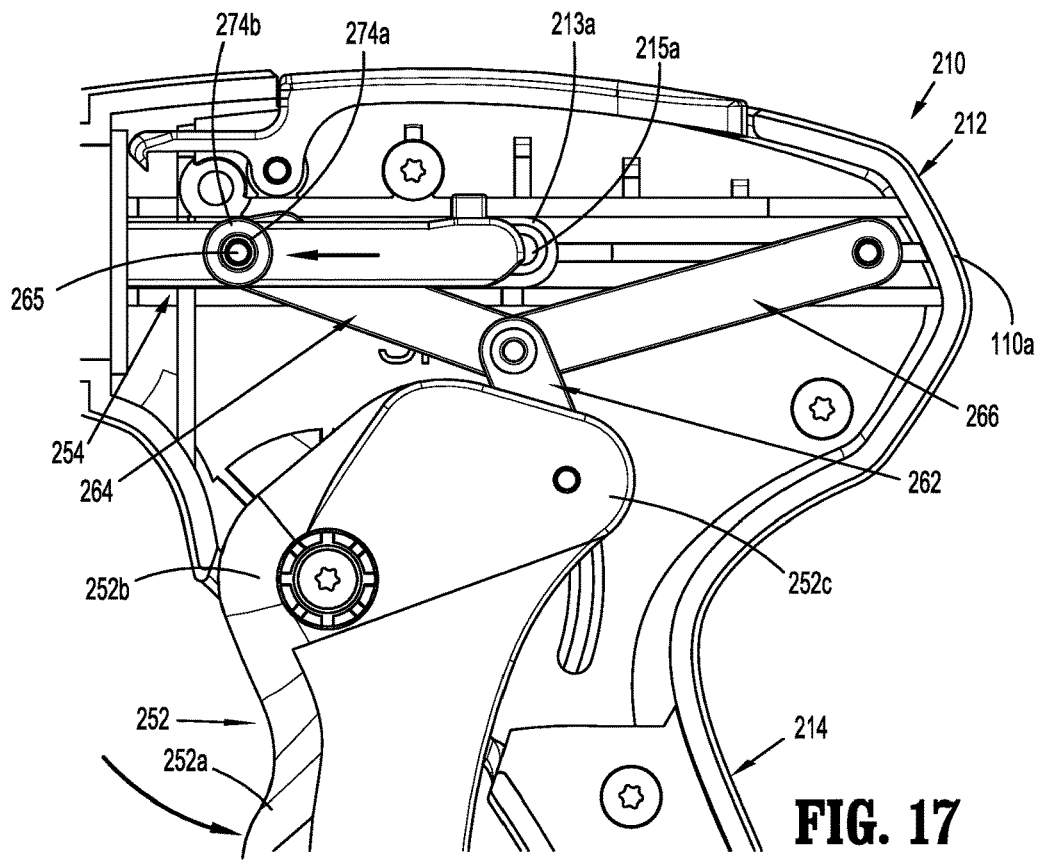
FIG. 17 is a side view of the handle assembly shown in FIG. 16, in a second or advanced condition.

In embodiments, the first sleeve bearing assembly 172 is positioned to facilitate initial movement of the linkage assembly 160. More particularly, the first sleeve bearing assembly 172 is positioned such that an initial force output from the second linkage member 164, as indicated by arrow "B" shown in FIG. 5, is tangent to the first sleeve bearing 172a. In this manner, the position of the first sleeve bearing assembly 172 facilitates initial rolling of the first sleeve bearing 172a. The second sleeve bearing assembly 174 is positioned such that a force output from the second linkage member 164, as indicated by arrow "C" shown in FIG. 6, is tangent to the second sleeve bearing 174a at the end of the firing cycle. The first sleeve bearing assembly 172 experiences a higher load at the beginning of the firing stroke and the second bearing assembly 174 experiences a higher load at the end of the firing stroke.

In embodiments, the first and second sleeve bearings 172, 174 are formed of polyether ether ketone (PEEK), nylon, other polymers, metal, or other suitable material.

Although shown as having only the first and second sleeve bearing assemblies 172, 174 supporting the drive member 154, it is envisioned that the friction reducing mechanism 170 may include more than two sleeve bearing assemblies (not shown).

In the same or another embodiment, the friction reducing mechanism 170 of the actuation assembly 150 of the handle assembly 100 may include a third sleeve bearing 176. The third sleeve bearing 176 is received about the pivot post 116 of the body portion 112 of the housing 110. As noted above, the intermediate pivot portion 152b of the trigger member 152 of the actuation mechanism 150 defines the pivot aperture 151 that receives the pivot post 116 of the housing 110. The third sleeve bearing 176 of the friction reducing mechanism 170 is disposed within the pivot aperture 151 in the trigger member 152 such that the third sleeve bearing 176 is positioned between the pivot post 116 of the body portion 112 and the trigger member 152.

In embodiments, the third sleeve bearing 176 is fixed relative to the pivot post 116 such that the trigger member 152 of the actuation assembly 150 rotates relative to the third bearing sleeve 176 and the pivot post 116. In another embodiment, the third bearing sleeve 176 is fixed relative to the trigger member 152 such that the trigger member 152 and the third sleeve bearing 176 rotate relative to the pivot post 116. In yet another embodiment, the third sleeve bearing 176 is neither fixed relative to the pivot post 116 nor the trigger member 152 such that the third sleeve bearing 176 rotates relative to either or both of the pivot post 116 and the trigger member 152.

In embodiments, the third sleeve bearing 176 is formed of stainless steel, PEEK, or other suitable material. The third sleeve bearing 176 reduces friction between the trigger member 152 and the body portion 112 of the housing 110, thereby reducing wear in the handle assembly 100.

With reference now to FIGS. 11-17, a handle assembly according to another embodiment of the present disclosure is shown generally as handle assembly 200. The handle assembly 200 is substantially similar to the handle assembly 100 described hereinabove, and will only be described in detail as relates to the differences therebetween.

The handle assembly 200 includes a housing 210, a latch assembly 220 (FIG. 11) operably disposed within housing 210, a rotation knob assembly 230 disposed on distal nose 212a of a body portion 212 of the housing 210, and an actuation mechanism 250 operably disposed within the housing 210.

The housing 210 of the handle assembly 200 is formed from first and second housing halves 210a, 210b (FIG. 15) that cooperate to define the body portion 212 and a fixed handle portion 214 depending from the body portion 212. The body portion 212 of housing 210 includes an internal pivot post 216 extending transversely within body portion 212.

The actuation mechanism 250 of the handle assembly 200 is operably supported by housing 210 and includes a trigger member 252, a drive member 254 operably connected to the drive member 254 by a linkage assembly 260, and a friction reducing mechanism 270. As described below, the friction reducing mechanism 270 reduces the friction in the handle assembly 200, and provides a smoother firing sequence and better mechanical advantage.

The trigger member 252 of the actuation mechanism 250 includes a grasping portion 252a, an intermediate pivot portion 252b, and a proximal extension 252c. The linkage assembly 260 includes a first linkage member 262, a second linkage member 264, and a third linkage member 266. The first linkage member 262 is pivotally coupled to the proximal extension 252c of the trigger member 252 towards a first end 262a of the first linkage member 262. The second and third linkages 264, 266 are each pivotally coupled to a second end 262b of the first linkage member 262 at first ends 264a, 266a of the respective second and third linkages 264, 266. A second end 264b of the second linkage member 264 is pivotally coupled to the drive member 254 by a pivot pin 265, while a second end 266b of the third linkage member 266 is pivotally coupled to the body portion 212 of the housing 210.

The pivot point between the first linkage member 262 and the proximal extension 252c of the trigger member 252, the pivot point between the first linkage member 262 and second and third linkages 264, 266, respectively, and the pivot point between the second linkage member 264 and the drive member 254, e.g., the pivot pin 265, are movable pivot points (e.g., movable relative to the housing 210), while the pivot point between the third linkage member 266 and the housing 210 is a fixed pivot point (e.g., fixed relative to the housing 210).

Upon actuation of the trigger member 252, e.g., proximal pivoting of the grasping portion 252a of the trigger member 252 towards the fixed handle portion 214 of the housing 210, the proximal extension 252c is moved in a counter-clockwise direction (from the orientation illustrated in FIG. 3), thereby urging the first linkage member 262 towards the drive member 254. This movement of the first linkage member 262 towards the drive member 254, in turn, urges the first ends 264a, 266a of the second and third linkages 264, 266, respectively, towards the drive member 254 to, in turn, urge the second end 264b of the second linkage member 264 distally such that the drive member 254 is translated distally through the body portion 212 of the housing 210. A biasing spring (not shown) may be provided to bias the trigger member 252 towards an initial or pre-actuated positon, thereby biasing the drive member 254 proximally.

The drive member 254 of the actuation assembly 250 is slidably disposed within the body portion 212 of the housing 210 in longitudinal alignment with the adapter assembly 20 (FIG. 1) when the adapter assembly 20 is engaged with the handle assembly 200. Distal sliding of the drive member 254 through the body portion 212 of the housing 210 during the firing stoke of the handle assembly 200 urges the drive member 254 into contact with a proximal portion (not shown) of an inner drive sleeve (not shown) of the elongate assembly 20 to translate the inner drive sleeve distally, e.g., to apply, form or close a surgical clip supported at end effector (not shown).

The friction reducing mechanism 270 of the actuation assembly 250 of the handle assembly 200 includes a bearing assembly 272. The bearing assembly 272 includes first and second inner sleeve bearings 274a, 276a and first and second outer sleeve bearings 274b, 276b supported about the pivot pin 265 of the actuation mechanism 250 that pivotally couples the second linkage member 264 to the drive member 254. The bearing assembly 272 of the friction reducing mechanism 270 facilitates distal movement of the drive member 254. More particularly, the first and second inner and outer sleeve bearings 274a, 274b, 276a, 276b are rotatably supported about the pivot pin 265 and ride within tracks 213a, 213b (FIG. 15) formed in the first and second housing halves 210a, 210b of the housing 210.

Each of the first and second housing halves 210a, 210b further define a slot 215a, 215b for accommodating the pivot pin 265 as the first and second inner and outer sleeve bearings 274a, 274b, 276a, 276b traverse the tracks 213a, 213b. The first and second ends of the slots 215a, 215b orient and constrain the movement of the drive member 254 during a firing stroke of the handle assembly 200. As the drive member 254 slides in a distal direction, the first and second inner and outer sleeve bearings 274a, 274b, 276a, 276b rotate about the pivot pin 265 to reduce the friction between the body portion 212 of the housing 210 and the drive member 254. The positioning of the bearing assembly 272 in alignment with the second linkage member 264 facilitates a smoother firing sequence and provides better mechanical advantage In embodiments, at least the bearing surfaces of the first and second housing halves 210a, 210b of the housing 210 of the handle assembly 200 are formed of PEEK or other suitable material. Similarly, either or both of the first and second inner and outer sleeve bearings 274a, 274b, 276a, 276b may be formed of PEEK or other suitable material.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A handle assembly, comprising:
a housing defining a longitudinal axis;
a trigger member operably coupled to the housing;
a drive member movable within the housing along the longitudinal axis;
a linkage assembly operably disposed within the housing and connecting the trigger member to the drive member, the linkage assembly including first, second, and third linkages, the linkage assembly being moveable between an initial condition and a fully-actuated condition; and
a friction reducing mechanism operably disposed within the housing relative to the drive member, the friction reducing mechanism including first and second bearing assemblies, the first bearing assembly including a first bearing sleeve disposed within the housing at a first fixed location and the second bearing assembly including a second bearing sleeve disposed within the housing at a second fixed location longitudinally spaced from the first fixed location, the first and second bearing sleeves being configured to facilitate movement of the drive member, wherein the first bearing assembly is positioned such that a longitudinal axis of the second linkage is tangent to the first bearing sleeve when the linkage assembly is in the initial condition and is tangent to the second bearing sleeve when the linkage assembly is in the fully-actuated condition.

2. The handle assembly of claim 1, wherein the first bearing assembly includes a first pivot pin and the second bearing assembly includes a second pivot pin, the first and second bearing sleeves being rotatably supported about the respective first and second pivot pins.

3. The handle assembly of claim 1, wherein the housing includes a pivot post and the friction reducing mechanism includes a third bearing sleeve, the third bearing sleeve being received about the pivot post between the pivot post and the trigger member to reduce friction between the housing and the trigger member during actuation of the handle assembly.

4. A handle assembly, comprising:
a housing defining a longitudinal axis;
a trigger member operably coupled to the housing;
a drive member movable within the housing along the longitudinal axis;
a linkage assembly operably disposed within the housing and connecting the trigger member to the drive member, the linkage assembly including first, second, and third linkages, the linkage assembly being moveable between an initial condition and a fully-actuated condition; and
a friction reducing mechanism operably disposed within the housing relative to the drive member, the friction reducing mechanism including a first bearing assembly in a first fixed location and second bearing assembly in a second fixed location longitudinally spaced from the first bearing assembly, the first bearing assembly including a first bearing sleeve rotatably disposed within the housing and the second bearing assembly including a second bearing sleeve rotatably disposed within the housing, the first and second bearing assemblies being configured to facilitate movement of the drive member, wherein the first bearing assembly is positioned such that a longitudinal axis of the second linkage is tangent to the first bearing sleeve when the linkage assembly is in the initial condition and the longitudinal axis of the second linkage is tangent to the second bearing sleeve when the linkage assembly is in the fully-actuated condition.

5. The handle assembly of claim 4, wherein the first bearing assembly includes a first pivot pin and the second bearing assembly includes a second pivot pin, the first and second bearing sleeves being rotatably supported about the respective first and second pivot pins.

6. The handle assembly of claim 4, wherein the housing includes a pivot post and the friction reducing mechanism includes a third bearing sleeve, the third bearing sleeve being received about the pivot post between the pivot post and the trigger member to reduce friction between the housing and the trigger member during actuation of the handle assembly.

7. A handle assembly, comprising:
a housing defining a longitudinal axis;
a trigger member operably coupled to the housing;
a drive member movable within the housing along the longitudinal axis;
a linkage assembly operably disposed within the housing on a first side of the drive member and connecting the trigger member to the drive member, the linkage assembly including first, second, and third linkages, the linkage assembly being moveable between an initial condition and a fully-actuated condition; and
a friction reducing mechanism operably disposed within the housing on a second, opposite side of the drive member, the friction reducing mechanism including first and second bearing assemblies configured to facilitate movement of the drive member, the first bearing assembly including a first bearing sleeve disposed within the housing and the second bearing assembly including a second bearing sleeve rotatably disposed within the housing, the first bearing assembly being located at a first fixed location and the second bearing assembly being located at a second fixed location longitudinally spaced from the first bearing assembly, wherein the first bearing assembly is positioned such that a longitudinal axis of the second linkage is tangent to the first bearing sleeve when the linkage assembly is in the initial condition and the longitudinal axis of the second linkage is tangent to the second bearing sleeve when the linkage assembly is in the fully-actuated condition.

8. The handle assembly of claim 7, wherein the first bearing assembly includes a first pivot pin and the second bearing assembly includes a second pivot pin, the first and second bearing sleeves being rotatably supported about the respective first and second pivot pins.

9. The handle assembly of claim 7, wherein the housing includes a pivot post and the friction reducing mechanism includes a third bearing sleeve, the third bearing sleeve being received about the pivot post between the pivot post and the trigger member to reduce friction between the housing and the trigger member during actuation of the handle assembly.

* * * * *